(12) United States Patent
Lalpuria et al.

(10) Patent No.: US 8,753,890 B2
(45) Date of Patent: Jun. 17, 2014

(54) APPARATUS AND METHOD USING ANTI-ADSORPTION AGENT TO FACILITATE SAMPLE MIXING AND ANALYSIS

(75) Inventors: Niten V. Lalpuria, Mumbai (IN); Darryn W. Unfricht, North Haven, CT (US); Igor Nikonorov, Whitestone, NY (US); Benjamin Ports, Hamden, CT (US); Douglas R. Olson, Pipersville, PA (US)

(73) Assignee: Abbott Point of Care, Inc., Princeton, NJ (US)

( * ) Notice: Subject to any disclaimer, the term of this patent is extended or adjusted under 35 U.S.C. 154(b) by 2 days.

(21) Appl. No.: 13/314,959

(22) Filed: Dec. 8, 2011

(65) Prior Publication Data

US 2012/0149118 A1 Jun. 14, 2012

Related U.S. Application Data

(60) Provisional application No. 61/421,451, filed on Dec. 9, 2010.

(51) Int. Cl.
*G01N 33/48* (2006.01)
*G01N 21/05* (2006.01)
*B01L 3/00* (2006.01)
*G01N 33/487* (2006.01)
*G01N 21/03* (2006.01)
*G01N 15/14* (2006.01)

(52) U.S. Cl.
CPC ......... *B01L 3/5027* (2013.01); *B01L 3/502707* (2013.01); *G01N 33/48* (2013.01); *G01N 33/487* (2013.01); *G01N 21/0303* (2013.01); *G01N 21/05* (2013.01); *G01N 15/1463* (2013.01); *G01N 15/1484* (2013.01); *B01L 2300/0816* (2013.01); *B01L 2300/165* (2013.01)

USPC ............ 436/63; 436/164; 436/165; 436/180; 422/502; 422/503; 422/554; 435/287.1; 435/287.3; 435/288.3; 435/288.4; 435/288.5

(58) Field of Classification Search
CPC .......... G01N 15/1463; G01N 15/1484; G01N 21/03; G01N 21/0303; G01N 21/05; G01N 33/48; G01N 33/487; G01N 33/49; G01N 1/10; B01L 3/00; B01L 3/5027; B01L 3/502707; B01L 2300/0816; B01L 2300/161; B01L 2300/165
USPC ................... 436/63, 164, 165, 166, 174, 180; 422/400, 401, 430, 68.1, 502, 503, 422/547, 554; 435/287.1, 287.3, 287.9, 435/288.3, 288.4, 288.5
See application file for complete search history.

(56) References Cited

U.S. PATENT DOCUMENTS

| | | | |
|---|---|---|---|
| 4,762,857 A | 8/1988 | Bollin, Jr. et al. | |
| 4,891,319 A | 1/1990 | Roser | |
| 5,242,792 A | 9/1993 | Rudolph et al. | |
| 5,627,037 A | 5/1997 | Ward et al. | |
| 5,902,565 A | 5/1999 | Cox et al. | |
| 6,635,226 B1 * | 10/2003 | Tso et al. | 422/129 |
| 6,890,512 B2 | 5/2005 | Roser et al. | |
| 6,929,953 B1 | 8/2005 | Wardlaw | |
| 7,329,538 B2 * | 2/2008 | Wainwright et al. | 435/288.7 |
| 2003/0224531 A1 * | 12/2003 | Brennen et al. | 436/180 |
| 2009/0075390 A1 | 3/2009 | Linder et al. | |
| 2010/0248273 A1 | 9/2010 | Campbell | |
| 2010/0291666 A1 | 11/2010 | Collier et al. | |
| 2011/0124132 A1 * | 5/2011 | Kim et al. | 436/525 |
| 2011/0244581 A1 * | 10/2011 | Nikonorov et al. | 436/43 |

FOREIGN PATENT DOCUMENTS

EP  1390750  3/2011

OTHER PUBLICATIONS

Kaushik et al., "Why is Trehalose an Exceptional Protein Stabilizer? An analysis of the thermal stability of proteins in the presence of the compatible osmolyte trehalose", The Journal of Biological Chemistry, vol. 278, No. 29, p. 26458-26465, 2003.

International Search Report for PCT/US2011/063981 dated Feb. 23, 2012.

Smilkov et al. "Biocompatible Zwitterionic Copolymer Networks with Controllable Swelling and Mechanical Characteristics of their Hydrogels", J Mater Sci: Mater Med (2008) 19:2389-2395.

* cited by examiner

*Primary Examiner* — Maureen Wallenhorst
(74) *Attorney, Agent, or Firm* — O'Shea Getz P.C.

(57) ABSTRACT

An apparatus and method for analyzing a biological fluid sample is provided. The method includes the steps of: a) providing an analysis cartridge having a channel and an analysis chamber, wherein the channel is in fluid communication with the analysis chamber and includes at least one hydrophobic interior wall surface; b) admixing one or more anti-adsorption agents with fluid sample disposed within the channel, wherein the anti-adsorption agents are operable to inhibit adsorption of fluid sample onto the interior wall surface of the channel; c) moving the fluid sample into the analysis chamber; and d) analyzing the sample within the analysis chamber.

11 Claims, 3 Drawing Sheets

US 8,753,890 B2

APPARATUS AND METHOD USING ANTI-ADSORPTION AGENT TO FACILITATE SAMPLE MIXING AND ANALYSIS

The present application is entitled to the benefit of and incorporates by reference essential subject matter disclosed in the U.S. Provisional Patent Application Ser. No. 61/421,451, filed Dec. 9, 2010.

BACKGROUND OF THE INVENTION

1. Technical Field

The present invention relates to apparatuses and methods for biological fluid analyses in general, and to the same in which a biological sample is mixed to produce a uniform distribution of constituents and/or reagents.

2. Background Information

Historically, biological fluid samples such as whole blood, urine, cerebrospinal fluid, body cavity fluids, etc. have had their particulate or cellular contents evaluated by smearing a small undiluted amount of the fluid on a slide and evaluating that smear under a microscope. Reasonable results can be gained from such a smear, but the cell integrity, accuracy and reliability of the data depends largely on the technician's experience and technique. Analysis by smear is also limited, and cannot be used for analyses such as a complete blood count (CBC).

In some instances, constituents within a biological fluid sample can be analyzed using impedance or optical flow cytometry. These techniques evaluate a flow of diluted fluid sample by passing the diluted flow through one or more orifices located relative to an impedance measuring device or an optical imaging device. Disadvantages of these techniques include that they require dilution of the sample, and fluid flow handling apparatus.

It is known that biological fluid samples such as whole blood that are quiescently held for more than a given period of time will begin "settling out", during which time constituents within the sample will deviate from the constituent distribution present within the collected sample; e.g., deviate from a uniform distribution of constituents within the sample. If the sample is quiescently held long enough, constituents within the sample can settle out completely and stratify (e.g., in a sample of whole blood, layers of white blood cells, red blood cells, and platelets can form within a quiescent sample). Non-uniformity within the sample can also occur when adsorption occurs within a fluid passage. The term "adsorption" as used herein refers to the tendency of fluid sample, or parts thereof, to adhere to the surfaces of a fluid passage. If a large enough population of constituents within a fluid sample (e.g., platelets, RBCs, WBCs in a sample of whole blood) adheres to a fluid passage between the point of collection and the chamber in which the sample will be analyzed, the sample available for analysis could be non-representative of the sample collected. In such instances, the accuracy of the analysis could be negatively affected.

In those embodiments where it is desirable to deposit one or more reagents within the cartridge for admixing with the sample, the reagents may be in a form (e.g., particulate form, crystalline form, low solubility, etc.) that inhibits dissolution with the sample. Undissolved particles of reagent above a certain size will not be admitted into the analysis chamber, but others may pass into the analysis chamber where they can appear as debris within the sample images. Large particles of dye, for example, can create localized high concentrations of dye, which concentrations can saturate cells and make them unidentifiable. In either instance, the concentration and uniformity of the reagent within the sample can be negatively affected.

What is needed is an apparatus and a method for analyzing biological fluid samples that facilitate sample uniformity, and/or reagent uniformity within the sample.

DISCLOSURE OF THE INVENTION

According to an aspect of the present invention, an analysis cartridge for biological fluid sample is provided that includes a housing and at least one anti-adsorption agent. The housing includes a channel and an analysis chamber. The channel is in fluid communication with the analysis chamber, and the channel includes one or more hydrophobic interior wall surfaces. The anti-adsorption agent(s) is provided with the housing in a manner such that it can be admixed with fluid sample at the time the sample is deposited in the housing, or subsequently during passage within the housing. The anti-adsorption agent is operable to be miscible with the fluid sample and operable to inhibit adsorption of the sample onto the interior wall surface of the channel.

According to another aspect of the present invention, a method for analyzing a biological fluid sample is provided. The method includes the steps of: a) providing an analysis cartridge having a channel and an analysis chamber, wherein the channel is in fluid communication with the analysis chamber and includes at least one hydrophobic interior wall surface; b) admixing one or more anti-adsorption agents with fluid sample disposed within the channel, wherein the anti-adsorption agents are operable to inhibit adsorption of fluid sample onto a wall surface of the channel; c) moving the fluid sample into the analysis chamber; and d) analyzing the sample within the analysis chamber.

According to another aspect of the present invention, an analysis cartridge for biological fluid sample is provided. The cartridge includes a housing and at least one dissolution additive. The housing has a channel and an analysis chamber. The channel is in fluid communication with the analysis chamber. The channel includes at least one hydrophobic wall surface. The dissolution additive(s) are provided with the housing in a manner such that it can be admixed with fluid sample at the time the sample is deposited in the housing, or subsequently during passage within the housing. The dissolution additive is miscible with the fluid sample and is operable to facilitate dissolution of at least one reagent into the fluid sample.

The features and advantages of the present invention will become apparent in light of the detailed description of the invention provided below, and as illustrated in the accompanying drawings.

DETAILED DESCRIPTION

Figure 1:
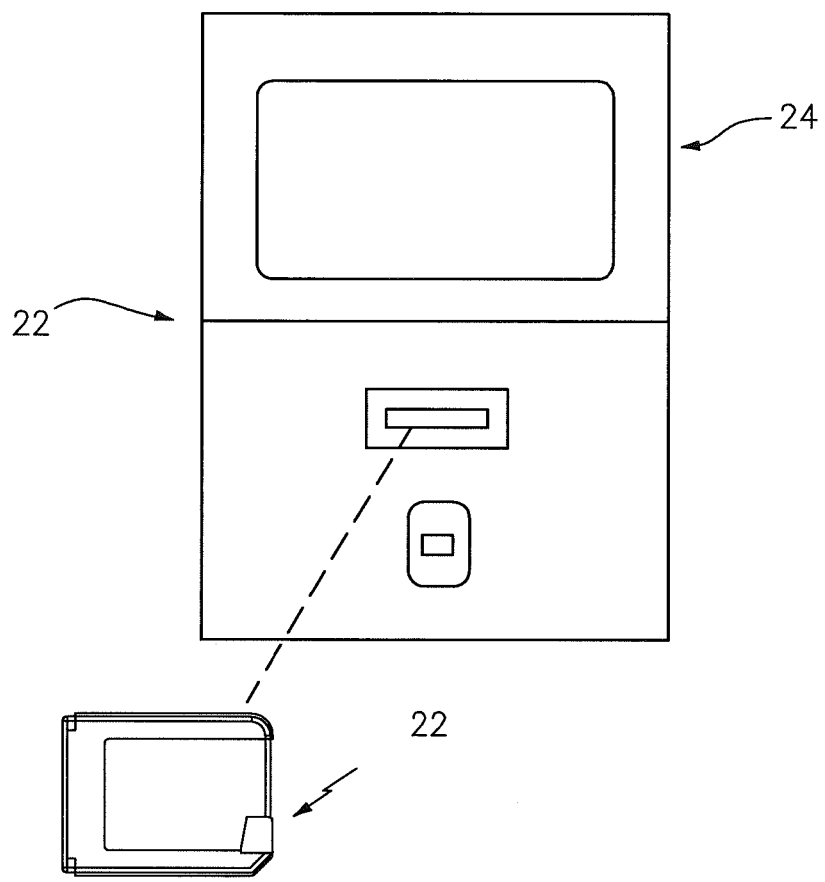
FIG. 1 illustrates a biological fluid analysis device.
Figure 2:
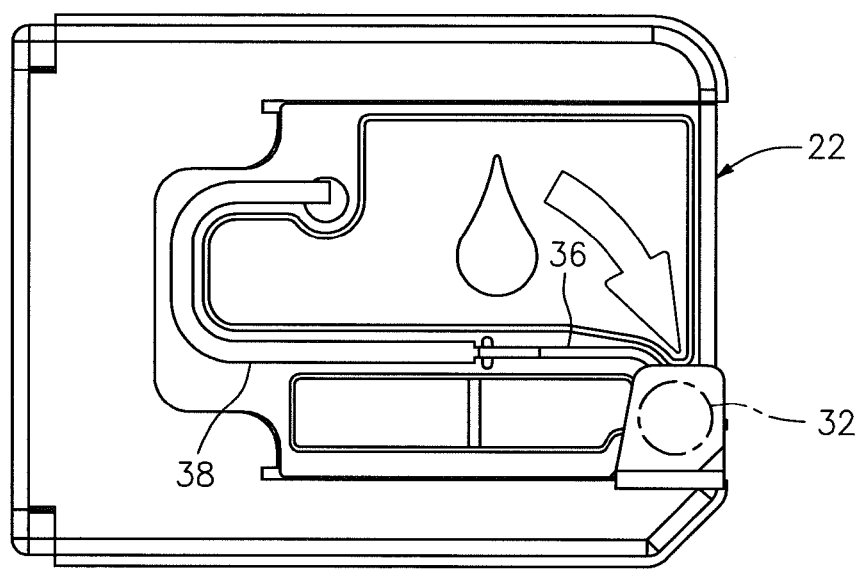
FIG. 2 is a diagrammatic planar view of a cartridge embodiment.

Referring to FIGS. 1-5, the present invention analysis system 20 includes a biological fluid sample cartridge 22 and an automated analysis device 24 for analyzing biological fluid samples such as whole blood. The automated analysis device 24 includes imaging hardware 26, a sample mixing system 28, and a programmable analyzer 30 for controlling the sample processing, imaging, and analyzing. The sample mixing system 28 is operable to manipulate a fluid sample to cause constituents within the sample to be at least substantially uniformly distributed within the sample prior to analysis of the sample. A sample analysis cartridge 22 is diagrammatically described below to illustrate the utility of the present invention. The present system 20 is not limited to any particular cartridge 22 embodiment. Examples of an acceptable cartridge 22 are described within U.S. patent application Ser. Nos. 12/971,860; 61/470,142; and 61/527,114, each of which is hereby incorporated by reference in its entirety. The present invention is not, however, limited to use with any particular cartridge 22.

The cartridge 22 described in U.S. patent application Ser. No. 12/971,860, which is an example of a cartridge used herein to facilitate description of the present apparatus and method, includes a fluid sample collection port 32, a valve 34, an initial channel 36, a secondary channel 38, a fluid driver port 40, and an analysis chamber 42. The collection port 32 is configured to collect the fluid sample (e.g., by finger prick, deposition by needle, etc.). The initial channel 36 is in fluid communication with the collection port 32 and is sized so that sample deposited within the collection port 32 is drawn into the initial channel 36 by capillary forces. The valve 34 is disposed in, or in communication with, the initial channel 36, near the end of the channel 36 engaged with the collection port 32 (in alternative cartridge embodiments no valve is required). The secondary channel 38 is in fluid communication with the initial channel 36, downstream of the initial channel 36. The geometry of the intersection between the initial channel 36 and the secondary channel 38 is such that fluid sample residing within the initial channel 36 will not be drawn by capillary force into the secondary channel 38. The secondary channel 38 is directly or indirectly in fluid communication with the analysis chamber 42. The analysis chamber 42 includes a pair of panels (at least one of which is transparent) separated by a distance, configured to receive a fluid sample there between for image analysis. The structure that provides the fluid communication between the secondary channel 38 and the analysis chamber 42 can assume a variety of different forms. In one embodiment, a metering channel extends between the secondary channel 38 and the analysis chamber 42, which metering channel is sized to draw fluid out of the secondary channel 38 by capillary action. In another embodiment, an ante-chamber 46 is disposed between, and is in fluid contact with both, the secondary channel 38 and an edge of analysis chamber 42 (e.g., see FIG. 3). Fluid sample within the secondary channel 38 can, for example, be moved into the ante-chamber 46 via pressure from the sample mixing system 28 or by gravity, etc. The above cartridge embodiments are offered to illustrate the utility and scope of the present cartridge. The present cartridge and method are not limited to these embodiments.

According to the present invention, one or more reagents (e.g., heparin, EDTA, dyes such as Acridine Orange, etc.) are deposited within the cartridge in one or more areas (e.g., fluid sample collection port 32, initial channel 36, secondary channel 38, analysis chamber 42, etc.). For example, an anticoagulant can be disposed within the collection port 32 to inhibit coagulation of the blood sample. For purposes of this disclosure, the term "reagent" is defined as including substances that interact with the sample, and dyes that add detectable coloration to the sample. As the sample fluid is drawn into and through the initial channel 36, the sample is at least partially admixed with the reagent initially disposed in the collection port 32.

In some embodiments of the present cartridge where more than one reagent is to be added to the sample, the order at which the sample traveling through the cartridge encounters the reagents is specifically chosen. For example, in those analyses where it is necessary or desirable to have the sample admix with reagent "A" before mixing with reagent "B", an appropriate amount of reagent "A" (e.g., an anticoagulant—EDTA) can be positioned upstream (e.g., in the initial channel 34) of an appropriate amount of reagent "B" (e.g., a dye disposed in the secondary channel 38). The distance between the reagent "A" and reagent "B" may be sufficient for reagent "A" to adequately mix with the sample prior to the introduction of reagent "B". Alternatively, as will be described below, the sample bolus can be cycled at the location of the reagent "A" prior to movement of the bolus to the position where reagent "B" is located. The cycling of the sample bolus can be accomplished using a bidirectional actuator to propel the bolus back and forth as will be described below. The aforesaid example is not intended to be limiting in any way. The positioning of the reagents within the fluid passages of the cartridge can be chosen, for example: a) to ensure that the pretreatment of a reagent is accomplished before subsequent interaction; b) to minimize or avoid competition between particular reagents for cellular interaction; and/or c) for those instances where the characteristics of a reagent are such that the reagent may need additional sample interaction time relative to other reagents.

In those embodiments where it is desirable to deposit one or more reagents within the cartridge 22 for admixing with the sample when deposited within the cartridge, one or more additives may be added to a reagent to facilitate the dissolution of that reagent within the sample. It is, for example, common for dyes (e.g., Acridine Orange—also referred to as "AcO" or Basic Orange 15; Astrazon Orange—also referred to as "AzO" or Basic Orange 21) to be added to the sample to facilitate analysis of the sample. As indicated above, it is our experience that during the deposition process, such dyes may be in a form that inhibits dissolution with the sample, consequently negatively affecting the concentration and uniformity of the dye within the sample. To avoid these problems, a dissolution additive is mixed with the dye (or other reagent) prior to depositing the dye within the cartridge. An example of an acceptable dissolution additive is trehalose. The dye and trehalose are mixed into a liquid solution and are deposited within the cartridge, where they are subsequently allowed to dry. It is understood that the molecular structure of the trehalose promotes uniform dye particle size and avoids large particle formation; e.g., the molecular structure of the trehalose is such that smaller dye particles distribute within the trehalose matrix thereby facilitating a more uniform dye particle distribution and inhibiting large dye particle formation. As an example, in an analysis of whole blood an acceptable amount of AcO dye (e.g., 1.8 µg) is added to a 20 µL test sample of whole blood (i.e., a dye concentration of 90 ng/µL). Favorable dye dissolution within the 20 µL whole blood sample can be achieved by initially depositing a mixture of greater than 0.9 µg of trehalose with the 1.8 µg of dye within a cartridge passage; e.g., a ratio of greater than 1:2 trehalose to dye. Current data suggests that the ratio of trehalose to dye can be as high as 8:1 with favorable results. Alternatively, for a same size whole blood sample (20 µL), favorable dye dissolution can be achieved by mixing an amount of EDTA (e.g., in the range of about 10-30 µg) with the 1.8 µg of dye. Another example of an acceptable dissolution additive is a substance comprising dendrimers.

In some embodiments of the present invention, reagents operable to impede adsorption of the sample on the surfaces within the cartridge 22 (e.g., fluid channel walls) are included. The fluid passages within the cartridge 22 can be formed of a material such as a plastic or a glass. The plastics typically used are hydrophobic in nature; e.g., polycarbonate ("PC"), polytetrafluoroethylene ("PTFE"), silicone, Tygon®, polypropylene, fluorinated ethylene polypylene ("FEP"), perfluouroalkoxy copolymer ("PFA"), cyclic olefin copolymer ("COC"), ethylene tetrafluoroethylene (ETFE), polyvinylidene fluoride, etc. In some applications, the fluid passages are coated to increase their hydrophobicity. An example of a hydrophobic material that can be applied as a coating is FluoroPel™ polymer solution available from Cytonix Corporation, of Beltsville, Md., U.S.A. When a substance like water passes through a passage formed in (and/or coated with) a hydrophobic material, water does not adsorb on the surfaces of the hydrophobic passage. Whole blood and other biological fluids containing proteins (referred to hereinafter collectively as "blood" for ease of description) behave differently from pure water, however, and adsorb to the hydrophobic passage walls. It is believed that the adsorption occurs, at least in part, because blood contains amphiphilic proteins such as Albumin, Immunoglobulin, and Fibrinogen. These proteins are "amphiphilic" because they have hydrophobic regions and hydrophilic regions. The hydrophobic regions can be readily adsorbed to a hydrophobic surface, at which time the hydrophilic regions are exposed (e.g., outwardly exposed). As a result, the once hydrophobic surface effectively becomes a hydrophilic surface. When subsequent blood flows over the hydrophilic surface, a layer is adsorbed onto the surface.

To overcome undesirable adsorption, embodiments of the present invention include an "anti-adsorption" reagent that when mixed with the sample decreases adsorption of sample on the passage walls. In the case of a whole blood sample analysis, a reagent that impedes the ability of proteins within the sample to adhere to the passage walls can be used. Surfactants and/or other reagents that make the amphiphilic proteins "less active" relative to a hydrophobic surface (i.e., less attracted to the channel surface) are desirable anti-adsorption reagents because they decrease the propensity of the proteins to adhere to the surface. It is believed that the surfactants coat the amphiphilic proteins and thereby make the proteins less active. For most whole blood analyses, the surfactant can be of a type that is non-hemolytic and/or used in a concentration that is non-hemolytic when mixed with the sample. In fact, surfactants are desirable for whole blood analyses because they can be effectively used in concentrations that do not result in lysing of RBCs. For those sample analyses where lysing is not an issue, a hemolytic reagent can be used.

More than one type of surfactant can be used as an anti-adsorption reagent. For example, non-ionic surfactants (e.g., Triton X-305 from Dow Chemical Co., Surfactant 10G from Dixie Chemical Co., Pluronic F-108 from BASF Corporation, and Tween-20, Tween-60, and/or Tween-80 from Roche Diagnostics from Mannheim, Germany) operate very favorably with a variety of different passage surface types (e.g., FluoroPel™ coating on a PC, FEP, PFA, ETFE, or polyvinylidene fluoride substrate). Concentrations of Triton-305 or Surfactant 10G™ at, or above, 0.1 ng/µL within a whole blood sample exhibit acceptable adsorption within a polycarbonate passage coated with FluoroPel™ coating. Similarly, concentrations of Tween-20™, Tween-60™, and Tween-80™, at, or above, 0.5 ng/µL within a whole blood sample exhibit acceptable adsorption within a polycarbonate passage coated with FluoroPel™ coating. Other non-ionic surfactants that produce acceptable adsorption when mixed with a whole blood sample include Triton X-100 and Triton X-705.

Zwitterionic surfactants such as 3-dimethyl (methacryloyloxyethyl) ammonium propane sulfonate (DMAPS) and 3-[(3-cholamidopropyl)dimethylammonio]-1-propane-sulfonate (CHAPS) can also be used as anti-adsorption agents. For example, concentrations of DMAPS or CHAPS at, or above, 0.05 ng/µL within a whole blood sample exhibit acceptable adsorption within a polycarbonate passage coated with FluoroPel™ coating.

Cationic surfactants (e.g., HDTAB) and anionic surfactants (e.g., sodium cholate hydrate, sodium deoxycholate) can also be used as anti-adsorption agents. Concentrations of any one of HDTAB, sodium cholate hydrate, or sodium deoxycholate at, or above, 0.05 ng/µL, within a whole blood sample exhibit acceptable adsorption within a polycarbonate passage coated with FluoroPel™ coating.

Disposing the appropriate amount of anti-adsorption reagent in an upstream passage (e.g., within the initial channel) rather than a downstream passage (e.g., the secondary channel) is advantageous, but not required for the operability of the present cartridge. Testing indicates that disposing the anti-adsorption reagent in an upstream passage (e.g., bowl, channels, initial channel, etc.) facilitates the movement of sample by capillary action or otherwise through the various passages, and also appears to help other reagents (e.g., EDTA) dissolve and enter solution with the sample.

Figure 4:
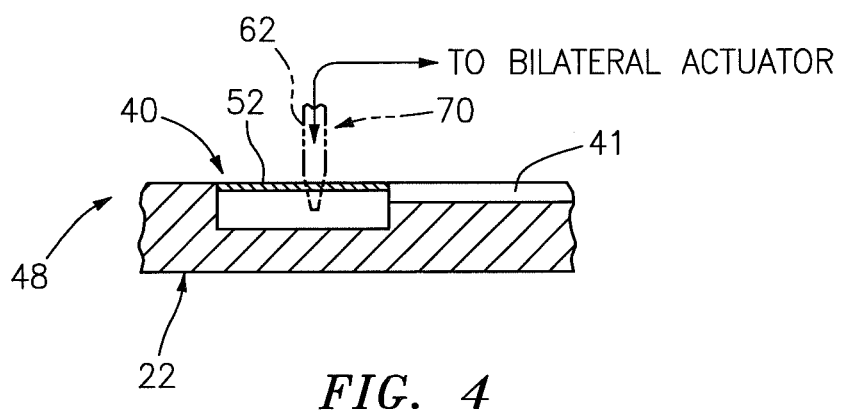
FIG. 4 is a diagrammatic sectional view of an embodiment of the present cartridge interface and the cartridge.

Referring to FIG. 4, the fluid driver port 40 is configured to engage the sample mixing system 28 and to permit pressurized fluid (e.g., air at positive and/or negative pressures) to access the cartridge 22 to cause the movement of fluid sample within cartridge 22. The fluid driver port 40 is in fluid communication with the initial channel 36 via channel 41 at a position 50 downstream of the valve 34. At that position 50, the valve 34 is operable to close off the collection port 32 from the fluid driver port 40. An example of a fluid driver port 40 is a cavity within the cartridge 22 covered by a cap 52 that includes a rupturable membrane operable to be pierced by a probe 70 of the sample mixing system 28. The probe 70 engaging the port 40 creates fluid communication between sample mixing system 28 and the channels within the cartridge 22. As indicated above, the present invention is not limited to use with the exemplary cartridge described herein to facilitate description of the present invention; e.g., the present invention may be used with cartridges that do not include a valve 34 or a driver port 40, or others that include different valve and/or driver port configurations.

Figure 5:
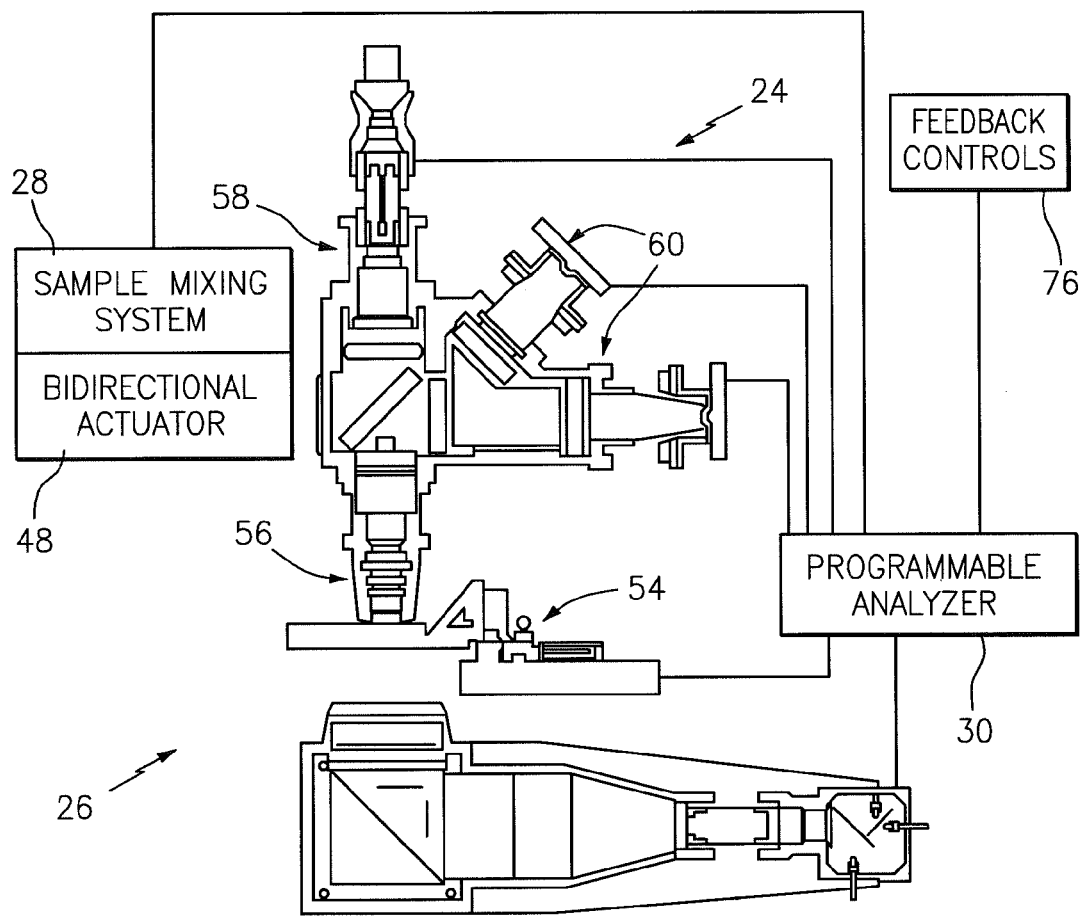
FIG. 5 is a schematic view of the present invention analysis system.

An example of an analysis device 24 that can be used with the present invention cartridge is schematically shown in FIG. 5, depicting its imaging hardware 26, a sample mixing system 28, a cartridge holding and manipulating device 54, a sample objective lens 56, a plurality of sample illuminators 58, and an image dissector 60. One or both of the objective lens 56 and cartridge holding device 54 are movable toward and away from each other to change a relative focal position. The sample illuminators 58 illuminate the sample using light along predetermined wavelengths. Light transmitted through the sample, or fluoresced from the sample, is captured using the image dissector 60, and a signal representative of the captured light is sent to the programmable analyzer 30, where it is processed into an image. The imaging hardware 26 described in U.S. Pat. No. 6,866,823 and U.S. patent application Ser. No. 13/204,415 (each of which is hereby incorporated by reference in its entirety) are acceptable types of imaging hardware 26 for the present analysis device 24. The present invention is not limited to use with the aforesaid imaging hardware 26, however.

The programmable analyzer 30 includes a central processing unit (CPU) and is in communication with the cartridge holding and manipulating device 54, the sample illuminator 58, the image dissector 60, and the sample mixing system 28. The CPU is adapted (e.g., programmed) to receive the signals and selectively perform the functions necessary to operate the cartridge holding and manipulating device 54, the sample illuminator 58, the image dissector 60, and the sample mixing system 28. It should be noted that the functionality of the programmable analyzer 30 may be implemented using hardware, software, firmware, or a combination thereof. A person skilled in the art would be able to program the unit to perform the functionality described herein without undue experimentation.

Figure 6:
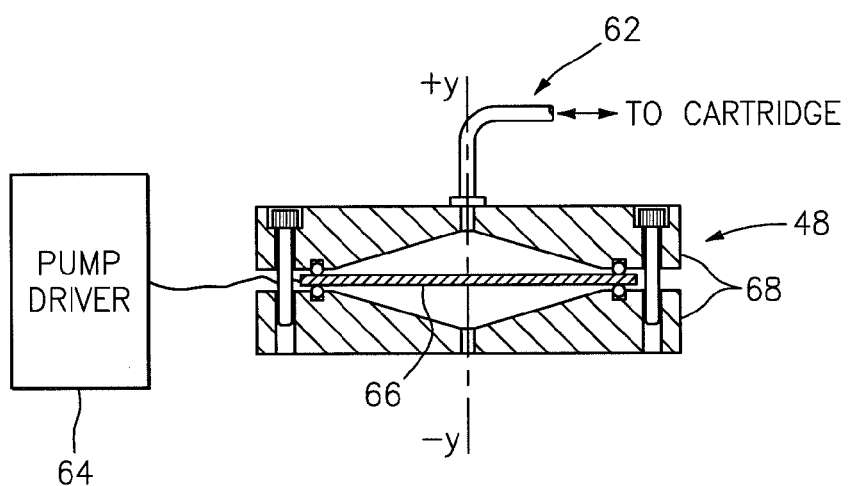
FIG. 6 is a schematic diagram of a piezo disk type of bilateral actuator.

Referring to FIGS. 4-6, the sample mixing system 28 includes a bidirectional actuator 48 and a cartridge interface 62. The bidirectional actuator 48 (shown schematically in FIG. 6) is operable to independently produce both a positive and a negative fluid displacement at one or more frequencies, which displacement can move sample within the cartridge. An example of an acceptable bidirectional actuator 48 is a piezo bending disk type actuator, utilized with a driver 64 for controlling the actuator 48. Piezo bending disk type actuators typically have a relatively fast response time, low hysteresis, low vibration, high linearity, and high reliability. In the embodiment shown in FIG. 6, the piezo bending disk type actuator includes a two-layer piezo bending disk 66 disposed in a housing 68. The two-layer piezo bending disk 66 is configured to create bending deflection in two opposing directions (e.g., -y, +y). Examples of a two-layer piezo bending disk 66 can be found in the T216-A4NO series offered by Piezo Systems, Inc., located in Cambridge, Mass., U.S.A. The present invention is not limited to piezo bending disk type actuators in general, and therefore not limited to these particular types of two layer piezo bending disks. The present invention is also not limited to a single fluid actuator that operates in a bidirectional manner; e.g., the present invention could be used with a system that utilizes a plurality of single-directional actuators, or combinations of single and bi-directional actuators.

The driver 64 is in communication with the bidirectional actuator 48 and is operable to control the actuator 48. The functionality of the driver 64 may be implemented using hardware, software, firmware, or a combination thereof. The driver 64 may be incorporated into the programmable analyzer 30, or may be a separate unit in communication with the programmable analyzer 30.

Figure 3:
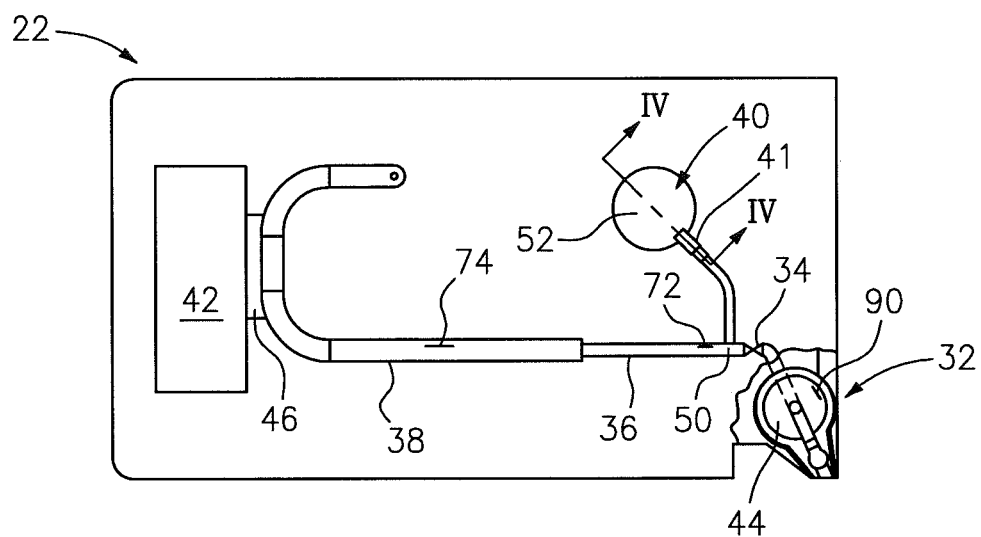
FIG. 3 is a diagrammatic sectional view of the cartridge embodiment.

Referring to FIGS. 3 and 4, the sample cartridge interface 62 includes fluid passage between the bidirectional actuator 48 and a probe 70 operable to engage the fluid driver port 40 of the cartridge 22. The interface 62 creates fluid communication between the bidirectional actuator 48 and the fluid driver port 40 of the cartridge 22. If the fluid driver port 40 has a cap 52 that includes a rupturable membrane, the probe 70 is operable to rupture the membrane and thereby provide fluid communication between the bidirectional actuator 48 and cartridge fluid driver port 40. The membrane, which is pierced by the probe 70, seals around the probe 70 to make the fluid path air tight. FIG. 4 diagrammatically illustrates this embodiment with a probe 70 shown in phantom. The present invention is not limited to the membrane/probe configuration, which is provided for illustration sake.

In the operation of the present system 20, a sample of biological fluid (e.g., whole blood) is deposited within the collection port 32 of the cartridge 22, and is subsequently drawn into the initial channel 36 of the cartridge 22 by capillary action, where it may reside for a period of time (e.g., the time between subject collection and sample analysis). The sample bolus will be drawn into the initial channel 36 by capillary forces until the leading edge of the sample bolus reaches the entrance to the secondary channel 38. In certain embodiments of the present cartridge 22, one or more reagents 72 may be disposed within the initial channel 36 and/or in the collection port 32. In those embodiments, as the sample is deposited in the cartridge 22 and travels within the initial channel 36, the reagents 72 are admixed with the sample. In those instances where the analysis of the sample is not performed immediately after sample collection, specific reagents (e.g., anticoagulants such as heparin or EDTA in a whole blood analysis) can be admixed with the sample to maintain the sample in an acceptable state (e.g., uncoagulated) for analysis.

Prior to the analysis being performed on the sample, the cartridge 22 is inserted into the analysis device 24 for analysis of the sample, the sample cartridge interface probe 70 engages the fluid driver port 40 of the cartridge 22, and the cartridge 22 configured to prevent fluid flow out of the cartridge 22 via the sample collection port 32; e.g., by actuating the valve closed. The specific order of these events can be arranged to suit the analysis at hand.

In the case of a whole blood sample that was collected and not immediately analyzed, constituents within the blood sample, RBCs, WBCs, platelets, and plasma, can settle and become stratified within the cartridge 22 over time. In such cases, there is considerable advantage in manipulating the sample prior to analysis so that the constituents become re-suspended in at least a substantially uniform state. In addition, in many applications there is also considerable advantage in uniformly mixing reagents with the sample. To create a uniform distribution of constituents and/or reagents within the sample, the analysis device 24 provides a signal to the bidirectional actuator 48 to provide positive and/or negative displacement of fluid (e.g., air) within the actuator 48 and connected cartridge passages to cause the sample bolus to move forward or backward (e.g., oscillate) within the initial channel 36. In terms of a piezo bending disk type embodiment of the bidirectional actuator 48, the analysis device 24 provides a signal to the driver 64, which in turn sends a high-voltage signal to the actuator 48 causing the disk 66 to deflect. Depending upon the desired action, the two-layer disk 66 may be operated to deflect and positively displace air and thereby move the sample bolus forward (i.e., in a direction toward the analysis chamber 42), or negatively displace air and thereby drawn the sample bolus backward (i.e., in a direction away from the analysis chamber 42), or to oscillate and cycle the sample bolus back and forth relative to a particular position.

The manner in which the sample bolus is manipulated within the cartridge 22 using the bidirectional actuator 48 can be selected to accommodate the analysis at hand. Using a whole blood sample analysis as an example, the sample residing within the initial channel 36 (already mixed with an anticoagulant to some degree) will likely have settled and constituents stratified to some degree prior to analysis. Initially, the bi-directional actuator 48 may be operated to pass the sample bolus between positions to verify the position of the sample, using the feedback controls 76. Once the location of the sample is verified, the sample may be cycled back and forth over a relatively short length to uniformly re-suspend constituents within the sample (and/or uniformly mix reagents). The frequency at which the sample is cycled and the "amplitude" of sample travel can be varied to suit the application at hand. The frequency and amplitude can be controlled by the selection of the bidirectional actuator and driver characteristics. At this point, the amount of manipulation may be selected to ensure that nothing more than an inconsequential (if any) amount of the sample bolus remains in the initial channel 36 when the sample is propelled further into the secondary channel 38. Once bidirectional actuator 48 is operated to move the sample bolus into the secondary channel 38, the sample may be more vigorously cycled to achieve the desired uniform distribution of constituents within the sample. Subsequently, the sample bolus may be driven to another position within the secondary channel 38 and cycled back and forth at that position to mix another reagent (e.g., dye 74) with the sample.

The velocity at which the sample is moved axially within the channels can have an effect on the amount of adsorption that occurs on the sample wall. In fluid channels having a hydrodynamic diameter in the range of 1.0 mm to 4.0 mm, it is our finding that a fluid sample velocity of not greater than about 20.0 mm/s is acceptable because it results in limited adsorption. A fluid sample velocity not greater than about 10.0 mm/s is preferred because it results in less adsorption. A fluid sample velocity within a range of between 1.0 mm/s and 5.0 mm/s is most preferred because it typically results in an inconsequential amount of adsorption.

Once the re-suspension and/or reagent mixing is complete, the bidirectional actuator 48 is operated to move the sample bolus to the portion of the secondary channel 38 in fluid communication with the analysis chamber 42. At that position, an amount of the sample bolus is drawn out of the secondary channel 38 where it can either be drawn or forced into the analysis chamber 42.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. An analysis cartridge for a biological fluid sample, comprising:
    a housing having a channel and an analysis chamber, wherein the channel is in fluid communication with the analysis chamber, and the channel includes at least one hydrophobic interior wall surface, wherein the analysis chamber includes a pair of panels configured to receive a fluid sample there between for image analysis, at least one of which panels is transparent;
    at least one anti-adsorption agent provided with the housing in a manner such that it can be admixed with fluid sample at the time the sample is deposited in the housing, or subsequently during passage within the housing, wherein the anti-adsorption agent is miscible with the fluid sample and is operable to inhibit adsorption of the sample onto an interior wall surface of the channel, and the anti-adsorption agent is disposed within the housing such that fluid sample received within the analysis chamber is mixed with the anti-adsorption agent; and
    a deposit of a mixture of a dye and dissolution additive, which mixture is disposed within the housing in a manner such that it can be admixed with fluid sample at the time the sample is deposited in the housing, or subsequently during passage within the housing, or both, wherein the dye and dissolution additive mixture is premixed prior to being disposed within the housing and which mixture is miscible with the fluid sample.

2. The cartridge of claim 1, wherein the dissolution additive includes trehalose.

3. The cartridge of claim 2, wherein the premixed mixture of dye and dissolution additive includes Acridine Orange (AcO) and trehalose in a ratio in the range of about 1:2 to 8:1, trehalose to AcO.

4. The cartridge of claim 1, wherein the dissolution additive includes at least one of EDTA or a substance containing dendrimers.

5. The cartridge of claim 4, wherein the premixed mixture of dye and dissolution additive includes Acridine Orange (AcO) and EDTA in a ratio in the range of about 5:1 to 15:1, EDTA to AcO.

6. A method for analyzing a biological fluid sample, comprising the steps of:
    providing an analysis cartridge having a channel and an analysis chamber, wherein the channel is in fluid communication with the analysis chamber and includes at least one hydrophobic wall surface, and wherein the analysis chamber includes a pair of panels configured to receive a fluid sample there between for image analysis, at least one of which panels is transparent;
    depositing a mixture of a dye and dissolution additive in the cartridge, wherein the dye and dissolution additive mixture is premixed prior to being disposed within the cartridge;
    admixing one or more anti-adsorption agents with fluid sample disposed within the channel, wherein the anti-adsorption agents are operable to inhibit adsorption of fluid sample onto an interior wall surface of the channel;
    moving the fluid sample into the analysis chamber;
    admixing the premixed dye and dissolution additive mixture with the fluid sample prior to moving the fluid sample into the analysis chamber, or admixing the premixed dye and dissolution additive mixture with the fluid sample within the analysis chamber, or both;
    imaging the fluid sample and dye and dissolution additive admixture residing within the analysis chamber to produce one or more images of the admixture; and
    analyzing the sample within the analysis chamber using the one or more images.

7. The method of claim 6, wherein the step of moving the fluid sample includes moving a bolus of sample at an axial velocity within the range of about 1.0 mm/sec to 5.0 mm/sec.

8. The method of claim 6, wherein the dissolution additive includes trehalose.

9. The method of claim 8, wherein the premixed mixture of dye and dissolution additive includes Acridine Orange (AcO) and trehalose in a ratio in the range of about 1:2 to 8:1, trehalose to AcO.

10. The method of claim 6, wherein the dissolution additive includes at least one of EDTA or a substance containing dendrimers.

11. The method of claim 10, wherein the premixed mixture of dye and dissolution additive includes Acridine Orange (AcO) and EDTA in a ratio in the range of about 5:1 to 15:1, EDTA to AcO.

* * * * *